| United States Patent [19] | [11] | 4,199,503 |
|---|---|---|
| Rentzea et al. | [45] | Apr. 22, 1980 |

[54] PHENYLAZOPHENYLOXYTRIAZOLYL COMPOUNDS

[75] Inventors: Costin Rentzea, Heidelberg; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 950,321

[22] Filed: Oct. 11, 1978

[30] Foreign Application Priority Data

Oct. 12, 1977 [DE] Fed. Rep. of Germany ....... 2745827

[51] Int. Cl.$^2$ ..................... C09B 45/22; C09B 27/00; A01N 9/20

[52] U.S. Cl. ................................ 260/146 R; 424/226; 260/157

[58] Field of Search ............................. 260/146 R, 157

[56] References Cited

U.S. PATENT DOCUMENTS

| 3,498,968 | 3/1970 | Dimroth et al. ..................... 260/206 |
| 3,981,885 | 9/1976 | Buchel et al. ......................... 260/157 |
| 3,984,392 | 10/1976 | van der Veen et al. .............. 260/206 |

OTHER PUBLICATIONS

Chemical Abstract, vol. 75, (1971), p. 118319n.

*Primary Examiner*—V. D. Turner
*Attorney, Agent, or Firm*—Keil & Witherspoon

[57] ABSTRACT

New substituted 1-(1,2,4-triazolyl-1)-1-(4'-phenylazo)-phenoxy-3,3-dimethylbutan-2-one compounds having a good fungicidal action, and fungicides containing these compounds as active ingredients.

2 Claims, No Drawings

PHENYLAZOPHENYLOXYTRIAZOLYL COMPOUNDS

The present invention relates to new and valuable substituted phenylazophenyloxytriazolyl-O,N-acetals and their salts and metal complex compounds, which have a good fungicidal action, fungicides containing these compounds, and a process for combating fungi with these compounds.

German Laid-Open Application DE-OS No. 2,063,857 discloses that 1-2-(2,4-dichlorophenyl)-2-(2-propenyloxy)-ethyl-1H-imidazole has a fungicidal action. Because its action is insufficient, particularly on mildews and rusts, it has little suitability for use as a crop protection agent for combating fungi.

We have now found that the new phenylazophenyloxytriazolyl-O,N-acetals of the formula

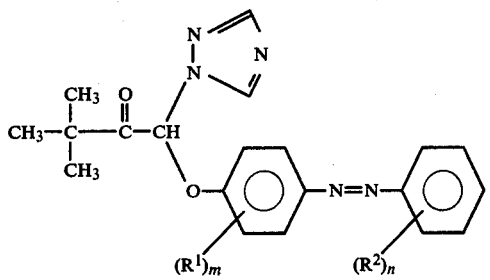

where $R^1$ and $R^2$ are identical or different and denote alkyl of a maximum of 4 carbon atoms, alkoxy of a maximum of 4 carbon atoms, alkylsulfoxy of a maximum of 4 carbon atoms, halogen (fluorine, chlorine, bromine and iodine), trifluoromethyl or nitro, m denotes one of the integers 0, 1, 2, 3 and 4, and n denotes one of the integers 0, 1, 2, 3, 4 and 5, and their salts and metal complex compounds, have a very good fungicidal action combined with excellent crop plant tolerance. Examples of salts are hydrochlorides, hydrobromides, sulfates, oxalates, dodecylbenzenesulfonates and nitrates.

The metal complex compounds have the formula

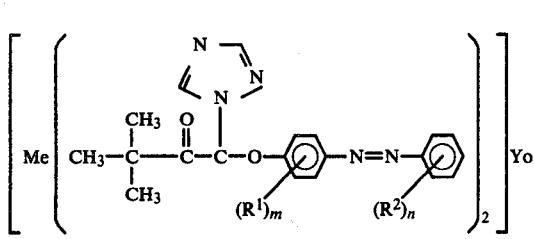

where Me denotes a metal cation, e.g., copper, zinc, tin, manganese, iron, cobalt and nickel, Y denotes the anion of an inorganic acid, e.g., hydrochloric acid, sulfuric acid, phosphoric acid, nitric acid and hydrobromic acid, and o denotes one of the integers 1, 2, 3 and 4.

We have further found that the new phenylazophenyloxy-(1,2,4-triazolyl-1)-O,N-acetals of the formula I are obtained by reaction of 1-(phenylazophenyloxy)-1-halo-3,3-dimethylbutan-2-one of the formula III with 1,2,4-triazole in a solvent in the presence of a basic catalyst:

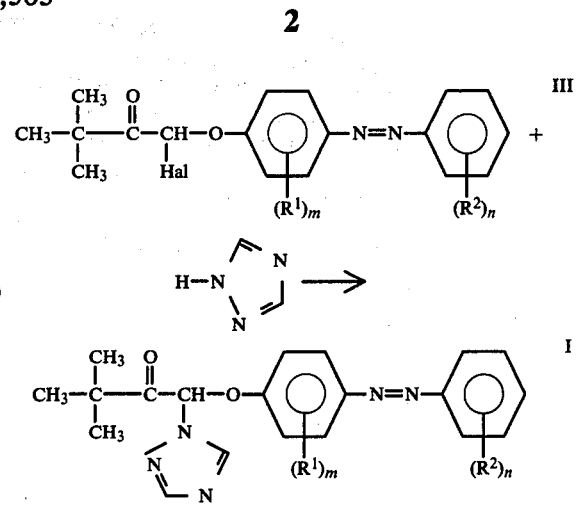

In formulae I and III, $R^1$, $R^2$, m and n have the above meanings.

The salts are prepared by reaction of a compound of the formula I with an acid, if desired in a solvent.

The metal complex compounds of the formula II are obtained by reaction of 1-(arylazoaryloxy)-1-(1,2,4-triazoyl-1)-N,O-acetals of the formula I with metal salts of the formula $$MeYo \cdot pH_2 \qquad\qquad IV,$$

where Me, Y and o have the above meanings and p denotes one of the integers 0, 1, 2, 3 and 4, in the presence of a solvent.

The compounds of the formula III used as starting materials may be obtained by conventional halogenation of 1-phenylazophenyloxy-3,3-dimethylbutan-2-ones of the formula V:

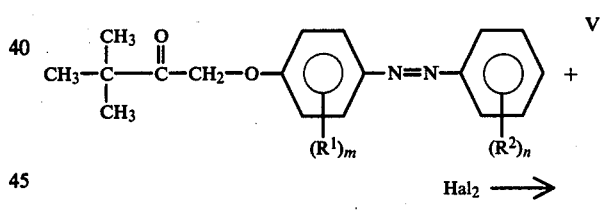
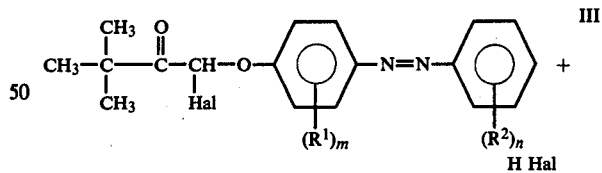

In these formulae, $R^1$, $R^2$, m and n have the above meanings and Hal denotes a halogen atom. Examples of halogenating agents which may be used are bromine, N-bromosuccinimide, sulfuryl chloride and N-chlorosuccinimide. Halogenation is advantageously carried out in an inert solvent such as $CH_2Cl_2$, $CHCl_3$, $CCl_4$ or 1,2-dichloroethane.

Advantageous solvents for the reaction with triazole to manufacture the 1-arylazoaryloxy-1-(triazolyl)-N,O-acetals of the formula I according to the invention are for example acetone, methyl ethyl ketone and acetonitrile. Basic catalysts which may be used are anhydrous inorganic salts, such as $K_2CO_3$ and $Na_2CO_3$, or organic bases, such as pyridine, triethylamine and N,N-dimethylcyclohexylamine. The reaction is best carried out at the boiling temperature of the solvent employed.

Suitable solvents for the manufacture of the metal complexes of the formula II are all water-miscible solvents. Methanol, ethanol and tetrahydrofuran are particularly suitable.

The reaction is generally carried out at from 10° to 50° C.

Individual examples of the new 1-(4-phenylazophenyloxy)-1-(1,2,4-triazoyl-1)-3,3-dimethylbutan-2-one derivatives are given below:

1-(1,2,4-triazolyl-(1))-1-(4'-phenylazo)-phenoxy-3,3-dimethylbutan-2-one
1-(1,2,4-triazolyl-(1))-1-(4'-(2''-fluorophenylazo)-phenoxy)-3,3-dimethylbutan-2-one
1-(1,2,4-triazolyl-(1))-1-(4'-(3''-fluorophenylazo)-phenoxy)-3,3-dimethylbutan-2-one
1-(1,2,4-triazolyl-(1))-1-(4'-(4''-fluorophenylazo)-phenoxy)-3,3-dimethylbutan-2-one
1-(1,2,4-triazolyl-(1))-1-(4'-(4''-chlorophenylazo)-phenoxy)-3,3-dimethylbutan-2-one
1-(1,2,4-triazolyl-(1))-1-(4'-(4''-bromophenylazo)-phenoxy)-3,3-dimethylbutan-2-one
1-(1,2,4-triazolyl-(1))-1-(4'-(2'',4''-dichlorophenylazo)-phenoxy)-3,3-dimethylbutan-2-one
1-(1,2,4-triazolyl-(1))-1-(4'-(3'',4''-dichlorophenylazo)-phenoxy)-3,3-dimethylbutan-2-one
1-(1,2,4-triazolyl-(1))-1-(4'-(2'',4'',5''-trichlorophenylazo)-phenoxy)-3,3-dimethylbutan-2-one
1-(1,2,4-triazolyl-(1))-1-(4'-(2'',4''-difluorophenylazo)-phenoxy)-3,3-dimethylbutan-2-one
1-(1,2,4-triazolyl-(1))-1-(4'-(3'',4''-difluorophenylazo)-phenoxy)-3,3-dimethylbutan-2-one
1-(1,2,4-triazolyl-(1))-1-(4'-(3''-chloro-4''-fluorophenylazo)-phenoxy)-3,3-dimethylbutan-2-one
1-(1,2,4-triazolyl-(1))-1-(4'-(3''-trifluoromethylphenylazo)-phenoxy)-3,3-dimethylbutan-2-one
1-(1,2,4-triazolyl-(1))-1-(4'-(2''-methyl-5''-chlorophenylazo)-phenoxy)-3,3-dimethylbutan-2-one
1-(1,2,4-triazolyl-(1))-1-(4'-(2''-chloro-4''-methylsulfoxyphenylazo)-phenoxy)-3,3-dimethylbutan-2-one
1-(1,2,4-triazolyl-(1))-1-(4'-(3''-chloro-4''-methoxyphenylazo)-phenoxy)-3,3-dimethylbutan-2-one
1-(1,2,4-triazolyl-(1))-1-(4'-(3''-chloro-4''-methoxyphenylazo)-phenoxy)-3,3-dimethylbutan-2-one
1-(1,2,4-triazolyl-(1))-1-(2'-chloro-4'-(phenylazo)-phenoxy)-3,3-dimethylbutan-2-one
1-(1,2,4-triazolyl-(1))-1-(2'-chloro-4'-(4''-fluorophenylazo)-phenoxy)-3,3-dimethylbutan-2-one
1-(1,2,4-triazolyl-(1))-1-(2'-chloro-4'-(4''-chlorophenylazo)-phenoxy)-3,3-dimethylbutan-2-one
1-(1,2,4-triazolyl-(1))-1-(2'-chloro-4'-(2'',4''-dichlorophenylazo)-phenoxy)-3,3-dimethylbutan-2-one.

Individual examples of metal complexes are as follows:

bis-(1-(1,2,4-triazolyl-(1))-1-(4'-(2''-fluorophenylazo)-phenoxy-3,3-dimethylbutan-2-one)-copper(II) chloride
bis-(1-(1,2,4-triazolyl-(1))-1-(4'-(3''-fluorophenylazo)-phenoxy-3,3-dimethylbutan-2-one)-copper(II) chloride
bis-(1-(1,2,4-triazolyl-(1))-1-(4'-(4''-fluorophenylazo)-phenoxy-3,3-dimethylbutan-2-one)-copper(II) chloride
bis-(1-(1,2,4-triazolyl-(1))-1-(4'-(4''-chlorophenylazo)-phenoxy-3,3-dimethylbutan-2-one)-copper(II) chloride
bis-(1-(1,2,4-triazolyl-(1))-1-(4'-(2'',4''-difluorophenylazo)-phenoxy-3,3-dimethylbutan-2-one)-copper(II) chloride
bis-(1-(1,2,4-triazolyl-(1))-1-(2'-chloro-4'-(4''-fluorophenylazo)-phenoxy-3,3-dimethylbutan-2-one)-copper(II) chloride
bis-(1-(1,2,4-triazolyl-(1))-1-(4'-(4''-fluorophenylazo)-phenoxy)-3,3-dimethylbutan-2-one)-zinc(II) chloride
bis-(1-(1,2,4-triazolyl-(1))-1-(4'-(2'',4''-dichlorophenylazo)-phenoxy-3,3-dimethylbutan-2-one)-zinc(II) chloride
bis-(1-(1,2,4-triazolyl-(1))-1-(4'-(3''-chloro-4''-fluorophenylazo)-phenoxy-3,3-dimethylbutan-2-one)-zinc(II) chloride
bis-(1-(1,2,4-triazolyl-(1))-1-(2'-chloro-4'-(4''-fluorophenylazo)-phenoxy-3,3-dimethylbutan-2-one)-zinc(II) chloride.

EXAMPLE 1

A. Reaction of

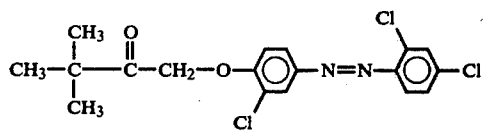

with N-bromosuccinimide to give

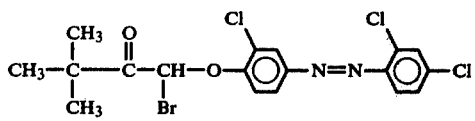

70 g of 1-(2'-chloro-4'-(2'',4''-dichlorophenylazo)-phenoxy)-3,3-dimethylbutan-2-one, 31.7 g of N-bromosuccinimide and 1 ml of bromine are stirred in 500 ml of carbon tetrachloride for 5 hours at 70° C. After the mixture has cooled it is filtered and the filtrate concentrated. The residue is washed with n-pentane.

Yield: 79.5 g (94% of theory); m.p.: 119°–123° C.

B. Reaction of

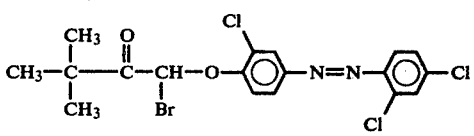

with 1,2,4-triazole to give

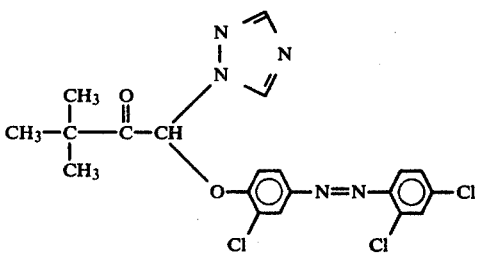

53 g of 1-(2'-chloro-4'-(2'',4''-dichlorophenylazo)-phenoxy)-1-bromo-3,3-dimethylbutan-2-one, 7.7 g of 1,2,4-triazole and 28 g of potassium carbonate are stirred, while boiling and refluxing, in 300 ml of acetone for 12 hours. After the mixture has cooled, it is filtered, the filtrate is concentrated, and the residue is separated by column chromatography on silica gel. The elution agents are cyclohexane and ethyl acetate; pale yellow crystals of the compound 1-(1,2,4-triazolyl-(1))-1-(2'-chloro-4-(2'',4''-dichlorophenylazo)-phenoxy)-3,3-dimethylbutan-2-one (compound no. 20) are obtained.

Yield: 19 g (37% of theory); m.p.: 168° C.

The compounds listed in Table 1 were prepared in the same way.

Table 1

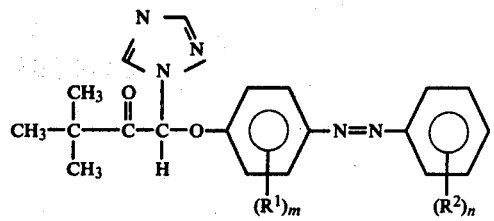

| Compound no. | $R^1$ | m | $R^2$ | n | m.p. °C. |
|---|---|---|---|---|---|
| 1 | — | 0 | — | 0 | 89–91 |
| 2 | — | 0 | 2-F | 1 | 71–75 |
| 3 | — | 0 | 3-F | 1 | 101–104 |
| 4 | — | 0 | 4-F | 1 | 104–105 |
| 5 | — | 0 | 4-Cl | 1 | 104–106 |
| 6 | — | 0 | 4-Br | 1 | 122–125 |
| 7 | — | 0 | 2,4-Cl$_2$ | 2 | 122–124 |
| 8 | — | 0 | 3,4-Cl$_2$ | 2 | 122–125 |
| 9 | — | 0 | 2,4,5-Cl$_3$ | 3 | 117–118 |
| 10 | — | 0 | 2,4-F$_2$ | 2 | 105–106 |
| 11 | — | 0 | 3,4-F$_2$ | 2 | 86–87 |
| 12 | — | 0 | 3-Cl 4-F | 2 | 116–120 |
| 13 | — | 0 | 3-CF$_3$ | 1 | 104–106 |
| 14 | — | 0 | 2-CH$_3$ 5-Cl | 2 | 102–108 |
| 15 | — | 0 | 2-Cl 4-SO$_2$CH$_3$ | 2 | 143–147 |
| 16 | — | 0 | 3-Cl 4-OCH$_3$ | 2 | 132–135 |
| 17 | 2-Cl | 1 | — | 0 | 108–110 |
| 18 | 2-Cl | 1 | 4-F | 1 | 105–107 |
| 19 | 2-Cl | 1 | 4-Cl | 1 | 134–136 |
| 20 | 2-Cl | 1 | 2,4-Cl$_2$ | 2 | 168 |
| 31 | 2-F | 1 | — | 0 | 110–112 |
| 32 | 2-F | 1 | 4-F | 1 | 90–92 |
| 33 | 2-Br | 1 | — | 0 | 117–119 |
| 34 | 2-Br | 1 | 4-F | 1 | 91–93 |

EXAMPLE 2

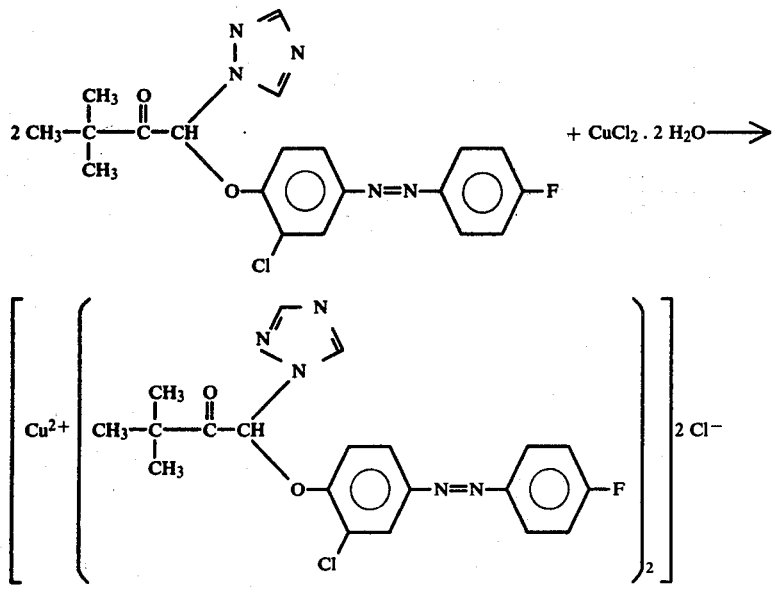

10 g of 1-(1,2,4-triazolyl-1)-1-(2'-chloro-4'-(4''-fluorophenylazo)-phenoxy)-3,3-dimethylbutan-2-one (compound no. 18) is dissolved at 40° C. in 200 ml of ethanol; a solution of 8.5 g of copper chloride dihydrate in 100 ml of ethanol is then added dropwise. After the mixture has stood overnight, the pale green crystals which have formed are filtered (compound no. 26).

Yield: 7 g; m.p.: 102°–104° C.

EXAMPLE 3

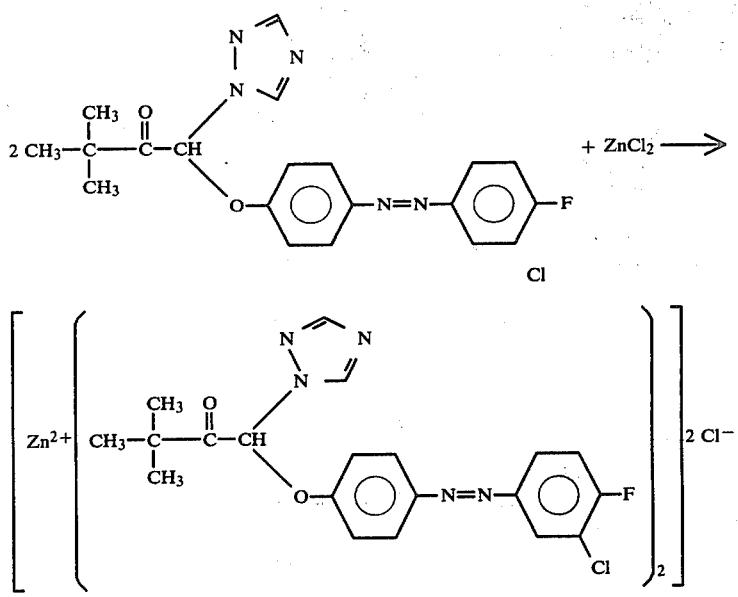

Table 2

[structure shown above table]

| Compound no. | Me | R¹ | m | R² | n | Y | o | m.p. °C. |
|---|---|---|---|---|---|---|---|---|
| 21 | Cu | — | 0 | 2-F | 1 | Cl | 2 | 105-110 |
| 22 | Cu | — | 0 | 3-F | 1 | Cl | 2 | 140-142 |
| 23 | Cu | — | 0 | 4-F | 1 | Cl | 2 | 103-105 |
| 24 | Cu | — | 0 | 4-Cl | 1 | Cl | 2 | 124-127 |
| 25 | Cu | — | 0 | 2,4-F₂ | 2 | Cl | 2 | 139-141 |
| 26 | Cu | 2-Cl | 1 | 4-F | 1 | Cl | 2 | 102-104 |
| 27 | Zn | — | 0 | 4-F | 1 | Cl | 2 | 168-171 |
| 28 | Zn | — | 0 | 2,4-Cl₂ | 2 | Cl | 2 | 174-176 |
| 29 | Zn | — | 0 | 3-Cl 4-F | 2 | Cl | 2 | 173-178 |
| 30 | Zn | 2-Cl | 1 | 4-F | 1 | Cl | 2 | 140-147 |

The compounds according to the invention and their salts and metal complex compounds have an excellent action on a broad spectrum of plant-pathogenic fungi, especially from the Ascomycetes and Basidiomycetes classes. Some of the agents according to the invention have a systemic action and may be used as foliar and soil fungicides, and particularly as seed disinfectants.

The fungicidal compounds are of considerable interest for combating numerous fungus diseases in various crop plants or their seed. By "crop plants", we mean in this connection especially wheat, rye, barley, oats, rice, Indian corn, cotton, soybeans, coffee, sugarcane, fruit and ornamentals in horticulture, and vegetables such as cucumbers, beans and Cucurbitaceae.

The new compounds are particularly suitable for combating the following plant diseases: *Erysiphe graminis* in cereals, *Erysiphe cichoriacearum* in Cucurbitaceae, *Podosphaera leucotricha* in apples, *Incinula necator* in graphes, *Erysiphe polygoni* in beans, *Sphaerotheca pannosa* in roses, Puccinia species in cereals, *Rhizoctonia solani* in cotton, Helminthosporium species in cereals, Ustilago species in cereals and sugarcane, and *Rhynchosporium secale* in cereals.

The compounds are applied by spraying or dusting the plants with the active ingredients, or by treating the seed with the active ingredients. The compounds may be applied before or after infection of the plants or the seed by fungi.

The compounds of the invention can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations in general contain from 0.1 to 95 percent by weight of active ingredient, preferably from 0.5 to 90 percent.

The formulation, and the ready-to-use preparations obtained therefrom, e.g. solutions, emulsions, suspensions, powders, dusts, pastes or granules, are applied in the conventional manner, e.g. by spraying, atomizing, dusting, treating seed, or watering.

The application rate depends on the type of effect desired, and is from 0.01 to 3, preferably from 0.01 to 1, kg of active ingredient per hectare.

The above ready-to-use preparations may contain other active ingredients together with those according to the invention, e.g. herbicides, insecticides, growth regulators and other fungicides or may be mixed with fertilizers and applied together with these. Mixture with other fungicides often broadens the spectrum of fungicidal action. The following list of fungicides with which the compounds according to the invention may be combined is intended to illustrate and not restrict the combination possibilities. Examples of fungicides which can be combined with the compounds of the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene-bis(thiocarbamoyl)-disulfide, zinc N,N'-propylene-bis-dithiocarbamate, and the ammonia complex of zinc N,N'-propylene-bis-dithiocarbamate and N-N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenylsulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodobenzoic acid anilide, 1-(3,4-dichloroanilino)-1-formylamino-2,2,2-trichloroethane, 2,6-dimethyl-N-tridecyl-morpholine and its salts, and 2,6-dimethyl-N-cyclododecyl-morpholine and its salts.

EXAMPLE 4

Action on wheat mildew

Leaves of wheat seedlings of the "Jubilar" variety grown in pots are sprayed with aqueous emulsions prepared from (dry basis) 80% (wt%) active ingredient and 20% emulsifier, and dusted, after the sprayed-on layer has dried, with spores of wheat mildew (*Erysiphe graminis* var. tritici). The plants are then placed in a greenhouse at from 20° to 22° C. and from 75 to 80% relative humidity. The extent of fungus spread is assessed after 10 days.

| Compound no. | Leaf attack after spraying with liquor containing active ingredient in amounts of | | |
|---|---|---|---|
| | 0.05% | 0.025% | 0.012% |
| 2 | 0 | 0 | 0 |
| 4 | 0 | 0 | 1 |
| 5 | 0 | 0 | 1 |
| 10 | 0 | 0 | 0 |
| 11 | 0 | 0 | 0 |
| 12 | 0 | 1 | 2 |
| 15 | 0 | 2 | 2–3 |
| 18 | 0 | 0 | 2 |
| 20 | 0 | 1 | 2 |
| 21 | 0 | 0 | 3 |
| 23 | 0 | 0 | 2 |
| 25 | 0 | 1 | 1 |
| 27 | 0 | 0 | 2 |
| 28 | 0 | 1 | 1–2 |
| 29 | 0 | 1 | 2–3 |
| Comparative agent | 2 | 3 | 3 |

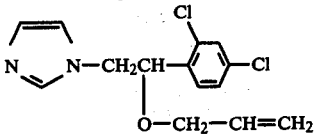

disclosed in DE-OS 2,063,857
Control (untreated) 5

0 = no damage, graduated down to 5 = total attack

EXAMPLE 5

Action on leaf rust of wheat

Leaves of pot-grown seedlings of the "Caribo" variety are dusted with spores of leaf rust (*Puccinia recondita*). The pots are then placed in a high humidity (90–95%) chamber at from 20° to 22° C. for 24 hours. During this time, the spores germinate and the germ tubes penetrate into the leaf tissue. The infected plants are then sprayed to run-off with aqueous liquors of 0.05, 0.025 and 0.012% strength by weight, the solids comprising 80% of active ingredient and 20% of ligninsulfonate. After the spray coating has dried, the test plants are set up in a greenhouse at from 20° to 22° C. and from 65 to 70% relative humidity. After 8 days, the degree of development of the rust fungi on the leaves is determined.

| Active ingredient no. | Leaf attack after spraying with liquor containing ... % of active ingredient | | |
|---|---|---|---|
| | 0.05 | 0.025 | 0.012 |
| 2 | 0 | 0 | 0 |
| 4 | 0 | 0 | 0 |
| 10 | 0 | 0 | 0 |
| 11 | 0 | 0 | 1 |
| 18 | 0 | 0 | 0 |
| 21 | 0 | 0 | 2 |
| 23 | 0 | 0 | 0 |
| 25 | 0 | 0 | 0 |
| 26 | 0 | 0 | 0 |
| 27 | 0 | 0 | 1 |
| 30 | 0 | 0 | 0 |
| Comparative agent | | | |

-continued

| Active ingredient no. | Leaf attack after spraying with liquor containing ... % of active ingredient | | |
|---|---|---|---|
| | 0.05 | 0.025 | 0.012 |
| ![structure: N⟋⟍N—CH₂—CH(—C₆H₃Cl₂)—O—CH₂—CH=CH₂] Cl, Cl, O—CH₂—CH=CH₂ | 3 | 4 | 5 |
| Control (untreated) | | 5 | |

0 = no damage, graduated down to 5 = total attack

EXAMPLE 6

Action on barley mildew

Leaves of barley seedlings grown in pots are sprayed with aqueous emulsions prepared from (dry basis) 80% (wt%) active ingredient and 20% emulsifier, and dusted, after the sprayed-on layer has dried, with spores of barley mildew (*Erysiphe graminis* var. hordei). The plants are then placed in a greenhouse at from 20° to 22° C. and from 75 to 80% relative humidity. The extent of fungus spread is assessed after 10 days.

| Active ingredient no. | Leaf attack after spraying with liquor containing active ingredient in amounts of | | |
|---|---|---|---|
| | 0.05% | 0.025% | 0.012% |
| 2 | 0 | 0 | 0 |
| 4 | 0 | 0 | 1 |
| 5 | 0 | 0 | 0 |
| 10 | 0 | 0 | 0 |
| 11 | 0 | 0 | 1 |
| 12 | 0 | 2 | 3 |
| 18 | 0 | 0 | 2 |
| 19 | 0 | 0 | 0 |
| 20 | 0 | 0 | 0 |
| 21 | 0 | 1 | 3 |
| 23 | 0 | 0 | 0 |
| 24 | 0 | 2 | 2–3 |
| 25 | 0 | 0 | 2 |
| 26 | 0 | 1 | 2 |
| 27 | 0 | 1 | 2 |
| 28 | 0 | 0 | 0 |
| 29 | 0 | 1 | 2 |
| 30 | 0 | 1 | 2 |
| Control (untreated) | | 5 | |

0 = no damage, graduated down to 5 = total attack

EXAMPLE 7

90 parts by weight of compound 1 is mixed with 10 parts by weight of N-methyl-α-pyrrolidone. A mixture is obtained which is suitable for application in the form of very fine drops.

EXAMPLE 8

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 10

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 12

3 parts by weight of compound 3 is intimately mixed with 97 parts by weight of particulate kaolin. A dust is obtained containing 3% by weight of the active ingredient.

EXAMPLE 13

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 14

40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 15

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

EXAMPLE 16

Action on cucumber mildew

Leaves of pot-grown cucumber seedlings are sprayed with aqueous emulsions, the solids comprising 80% of active ingredient and 20% of emulsifier, and dusted, after the sprayed-on layer has dried, with spores of cucumber mildew (*Erysiphe cichoriacearum*). The plants are then placed in a greenhouse at from 20° to 22° C. and from 75 to 80% relative humidity. The extent of fungus development is determined after 10 days.

| | Leaf attack after spraying with liquor containing active ingredient in amounts of | | |
|---|---|---|---|
| Active ingredient | 0.05% | 0.025% | 0.0125% |
| 3 | 0 | 0 | 0 |
| Control (untreated) | 5 | | |

0 = no attack, graduated down to 5 = total attack.

We claim:

1. A 1-(1,2,4-triazolyl-1)-1-(4'-phenylazo)-phenyloxy-3,3-dimethylbutan-2-one compound of the formula

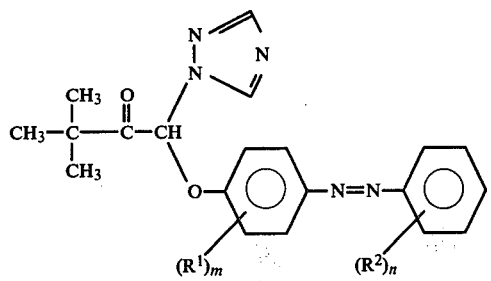

where R¹ and R² are identical or different and denote alkyl of a maximum of 4 carbon atoms, alkoxy of a maximum of 4 carbon atoms, alkylsulfoxy of a maximum of 4 carbon atoms, halogen, trifluoromethyl or nitro, m denotes one of the integers 0, 1, 2, 3 and 4, and n denotes one of the integers 0, 1, 2, 3, 4 and 5, a salt thereof or a metal complex of the formula

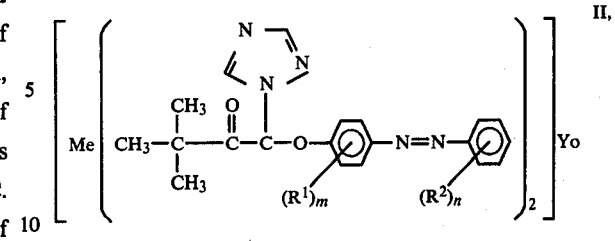

where Me is a copper, zinc, tin, manganese, iron, cobalt or nickel cation; Y is an anion of an inorganic acid; and 0 is the integer 1, 2, 3 or 4.

2. A 1-(1,2,4-triazolyl-1)-1-(4'-phenylazo)-phenyloxy-3,3-dimethylbutan-2-one compound selected from the group consisting of

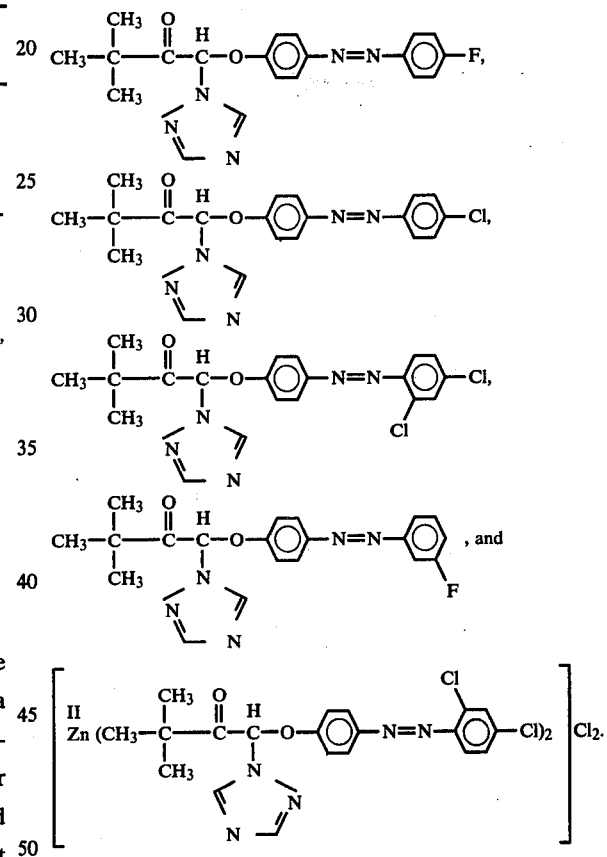

* * * * *